US009526716B2

(12) United States Patent
Bombardelli

(10) Patent No.: US 9,526,716 B2
(45) Date of Patent: Dec. 27, 2016

(54) COMPOSITIONS FOR THE TREATMENT OF PERIPHERAL ULCERS OF VARIOUS ORIGINS

(71) Applicant: INDENA S.P.A., Milan (IT)

(72) Inventor: Ezio Bombardelli, Groppello Cairoli (IT)

(73) Assignee: INDENA S.P.A., Milan (IT)

( * ) Notice: Subject to any disclaimer, the term of this patent is extended or adjusted under 35 U.S.C. 154(b) by 0 days.

(21) Appl. No.: 14/935,036

(22) Filed: Nov. 6, 2015

(65) Prior Publication Data

US 2016/0058812 A1   Mar. 3, 2016

Related U.S. Application Data

(63) Continuation of application No. 14/342,618, filed as application No. PCT/EP2012/067893 on Sep. 13, 2012, now Pat. No. 9,278,084.

(30) Foreign Application Priority Data

Sep. 16, 2011  (IT) .............................. MI2011A1671

(51) Int. Cl.
| | | |
|---|---|---|
| *A61K 36/00* | (2006.01) | |
| *A61K 31/353* | (2006.01) | |
| *A61K 36/28* | (2006.01) | |
| *A61K 36/87* | (2006.01) | |
| *A61K 31/352* | (2006.01) | |
| *A61K 31/7048* | (2006.01) | |
| *A61K 36/185* | (2006.01) | |
| *A61K 36/35* | (2006.01) | |
| *A61K 36/45* | (2006.01) | |
| *A61K 9/00* | (2006.01) | |
| *A61K 47/10* | (2006.01) | |
| *A61K 9/06* | (2006.01) | |
| *A61K 9/107* | (2006.01) | |
| *A61K 45/06* | (2006.01) | |

(52) U.S. Cl.
CPC ........... *A61K 31/353* (2013.01); *A61K 9/0014* (2013.01); *A61K 9/06* (2013.01); *A61K 9/107* (2013.01); *A61K 31/352* (2013.01); *A61K 31/7048* (2013.01); *A61K 36/185* (2013.01); *A61K 36/28* (2013.01); *A61K 36/35* (2013.01); *A61K 36/45* (2013.01); *A61K 36/87* (2013.01); *A61K 45/06* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 4,258,055 | A | 3/1981 | Lietti et al. |
| 4,376,781 | A | 3/1983 | Lietti et al. |
| 5,200,186 | A | 4/1993 | Gabetta et al. |
| 6,224,871 | B1 | 5/2001 | Hastings et al. |
| 6,780,442 | B2 | 8/2004 | Bailey et al. |
| 7,763,289 | B2 | 7/2010 | Bommarito |
| 2003/0152610 | A1 | 8/2003 | Rolf et al. |
| 2005/0053677 | A1 | 3/2005 | Greene |
| 2005/0100622 | A1 | 5/2005 | Nair et al. |
| 2007/0025645 | A1 | 2/2007 | Slatter |
| 2007/0104728 | A1 | 5/2007 | Rangel |

FOREIGN PATENT DOCUMENTS

| | | |
|---|---|---|
| EP | 0210785 B1 | 2/1987 |
| EP | 0412300 B1 | 2/1991 |
| EP | 0573777 B1 | 1/1993 |
| WO | 0217732 A2 | 3/2002 |
| WO | 2006063716 A1 | 6/2006 |

OTHER PUBLICATIONS

Health and Nutrition Tips: Bilberry Complex, Online URL>http://www.healthandnutritiontips.net/bilberry_complex/bilberry_complex.html> archived to Nov. 4, 2010 with archive.org, four pages, legible text format.
International Preliminary Report on Patentability issued in counterpart PCT Application No. PCT/EP2012/067893.
International Search Report issued in counterpart PCT Application No. PCT/EP2012/067893.
Martin-Aragon, S., et al., "Antioxidant action of vaccinium myrtillus L.," Phytotherapy Research, vol. 12, pp. S104-S106, 1998.
Muller et al., "High performance liquid chromatography analysis of anthocyanins in bilberries (*Vaccinium myrtillus* L.), Blueberries (*Vaccinium corymbosum* L.) and corresponding Juices", Journal of Food Science, vol. 77, No. 4, 2012 pp. C340-C345.
Nayak, BS, et al., "Wound-healing properties of oils . . . ", Phytotherapy Research, vol. 25, No. 8, pp. 1201-1208, 2011.
Onslow, The Anthocyanins Pigments of Plants, Second Ed. University Press, 1925, pp. 56-57.
Speroni, E., et al., "Anti-inflammatory and cicatrizing . . . " Journal of Ethnopharmacology, Elsevier Scientific Publishers Ltd, vol. 79, No. 2, pp. 265-272, 2002.
Written Opinion of International Searching Authority issued in counterpart PCT Application No. PCT/EP2012/067893.

*Primary Examiner* — Qiuwen Mi
(74) *Attorney, Agent, or Firm* — Silvia Salvadori, P.C.; Silvia Salvadori

(57) ABSTRACT

The present invention relates to combinations of an agent that stimulates cell proliferation and an anti-inflammatory/analgesic, which are useful in the treatment of peripheral ulcers of various origins, such as radiation dermatitis, diabetic ulcers, ulcers caused by venous stasis of the limbs, bedsores, and the associated skin infections, proctitis, vulvovaginitis and haemorrhoids with vascular lesions. These combinations can be presented as formulations for topical use.

4 Claims, No Drawings

COMPOSITIONS FOR THE TREATMENT OF PERIPHERAL ULCERS OF VARIOUS ORIGINS

This U.S. non-provisional application is a continuation of U.S. application Ser. No. 14/342,618 filed on Mar. 20, 2014, which is a U.S. National Stage of PCT/EP2012/067893 filed on Sep. 13, 2012, which claims priority to and the benefit of Italian Application No. MI2011A001671 filed on Sep. 16, 2011, the contents of which are all incorporated by reference in their entireties.

The present invention relates to bisulphite adducts of pure anthocyanosides or extracts containing them for use as topical medicaments in the treatment of ulcers and wounds.

The invention also relates to compositions containing said bisulphite adducts as cell-proliferation-stimulating agents in association with anti-inflammatories/analgesics. The compositions according to the invention are useful in the treatment of radiation dermatitis, burns, peripheral ulcers of various origins, such as diabetic ulcers, ulcers caused by venous stasis of the limbs, bedsores, and the associated skin infections.

More particularly, the invention relates to compositions containing bisulphite adducts of pure anthocyanosides or extracts containing them, and extracts of *Echinacea* sp. The compositions can optionally also contain other active ingredients, such as natural or synthetic vasokinetics.

TECHNICAL BACKGROUND

Peripheral ulcers, whether they are of traumatic or metabolic origin, such as diabetic ulcers or those caused by venous stasis of the limbs, bedsores and the associated skin infections, have different etiologies, although they have some symptoms in common. Some involve the peripheral microcirculation and circulation, and are mainly connected with arteriosclerosis, which causes occlusion of the medium and small arteries with consequent oedema which, due to accidental causes or scratching as a result of itching, can lead to a lesion that is slow to heal due to subsequent bacterial and/or fungal infection. Other ulcers, such as those caused by radiation or thermal or mechanical damage, and bedsores, have a definite origin.

Ulcers associated with chronic venous insufficiency require long-term treatment with combinations of substances which have different, synergic actions. Diabetic ulcers have similar origins to the former, and are accompanied by peripheral pain and purpura. Ulcers of traumatic origin have a strong antalgic component.

Vasokinetics and vasoprotectors in general improve wound healing, especially in the case of bedsores, although they alone are unable to heal the wound. The need is therefore felt for pharmacological treatments that combine a wound-healing and vasokinetic action with an analgesic and antiseptic/antibacterial action.

Keeping the arterial microcirculation active and removing protein seepage from the ulcerated area by means of lymph drainage further accelerates tissue re-epithelialisation.

DESCRIPTION OF THE INVENTION

It has been found that bisulphite adducts of anthocyanosides in pure form or extracts containing them possess better biological activity than the initial anthocyanoside.

It has also been found that the combination of said bisulphite adducts of anthocyanosides with lipophilic extracts of *Echinacea* sp induces surprisingly rapid wound-healing, with a reduction in the surrounding oedema and re-epithelialisation, due to the immediate reduction in fibrin production and protein seepage, which allows cleansing of the sore and rapid proliferation of granulation tissue.

The present invention therefore relates to compositions containing, as active ingredients:
 a) bisulphite adducts of anthocyanosides in pure form or of extracts containing them,
 b) lipophilic extract of *Echinacea* sp,
 and optionally
 c) substances with a vasokinetic action.

The compositions according to the invention are useful in the treatment of peripheral ulcers of various origins, such as radiation dermatitis, burns, haemorrhoids, stasis or diabetic ulcers, bedsores, and the associated skin infections.

Substances with an anthocyanin backbone are well-known to possess in vitro activity on fibroblast proliferation, antiprotease activity on the ground substance of connective tissue, and vasokinetic activity at venous and lymphatic level. However, these compounds are unsuitable for topical administration because they cause undesirable, unacceptable staining of the ulcers and the proximal tissue. Sulphur dioxide and bisulphite are known to interact with the bases of oxonium to give a colourless compound generating the following adducts:

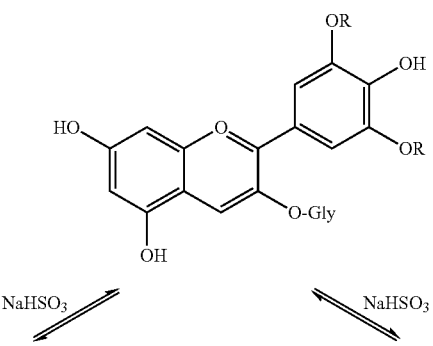

-continued

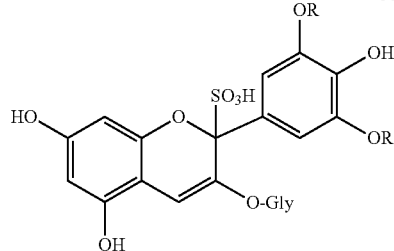 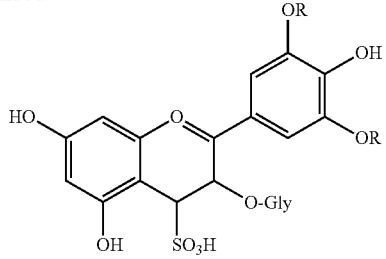

where R is hydrogen or methyl.

The use of said adducts in pharmaceutical formulations explains their considerable antibacterial and antifungal activity, which allows the elimination of antimicrobial stabilisers. The bisulphite adducts are balanced with the anthocyanin compounds, but do not stain the tissue with which they come into contact.

According to the present invention, said adducts can be formed directly in the formulation by mixing anthocyanins/anthocyanosides with sulphites such as sodium metabisulphite. The adducts can be present in isolated form, or in the form of extracts containing them. When present in the form of extracts, the following will preferably be used: *Ericaceae* extracts, preferably from *Vaccinium* sp, such as *Vaccinium myrtillus, Vaccinium erythrocarpon, Vaccinium macrocarpon, Vaccinium microcarpum* and *Vaccinium oxycoccos, Saxifragaceae* extracts, preferably *Ribes nigrum, Vitaceae* extracts, preferably *Vitis vinifera, Caprifoliaceae* extracts, preferably *Sambucus nigra*, and *Elaeocarpaceae* extracts, preferably *Aristotelia chilensis*.

Extracts of the ripe fruit of *Vaccinium myrtillus, Vitis vinifera, Ribes nigrum* or *Sambucus nigra* are preferred.

The term anthocyanosides comprises both anthocyanosides properly so called and their aglycons (anthocyanidins).

According to a preferred aspect, the anthocyanosides preferably derive from bilberry (*Vaccinium myrtillus*) extracts. Bilberry extracts are known to have a marked wound-healing activity, with the result that they have been used in the treatment of gastric and duodenal ulcers, and a marked anti-inflammatory action, especially at topical level, due to their activity on capillary permeability and fragility. Bilberry anthocyanosides also have a bacteriostatic and antiviral action.

The preparation of bilberry extracts containing anthocyanosides is known.

The lipophilic extract of *Echinacea* exercises an analgesic, antiviral and anti-inflammatory activity which produces a global improvement in wound-healing; it also has a significant effect on all forms of itching, a condition that often accompanies the formation of sores caused by venostasis, and is useful in the healing, and above all prevention, of sores. The analgesic effect due to the isobutylamide component is associated with its interaction with cannabinoid receptors CB1 and CB2 and activation of the vanilloids.

According to a preferred aspect of the invention, the lipophilic extract of*Echinacea* sp. is a lipophilic extract of *Echinacea angustifolia* or *purpurea*.

The percentages of active ingredients can range from 0.05 to 2% for catechin polyphenols or anthocyanosides, or extracts containing them, and from 0.01 to 1% for lipophilic extract of *Echinacea* sp.

A vasokinetic agent selected from visnadine or esculoside is preferably added for the treatment of bedsores.

The compositions according to the invention will preferably contain the active components in the following percentage intervals:
 a) bisulphite adducts of anthocyanosides or extracts containing them: 0.05 to 2%, preferably 0.5 to 1%;
 b) lipophilic extract of *Echinacea* sp.: 0.01 to 1%, preferably 0.05 to 0.3%;
 and optionally
 c) visnadine or esculoside from 0.2 to 1%, preferably visnadine in the percentage of 0.5%.

The bisulphite adducts are formed by adding to the anthocyanins or extracts containing them a bisulphite in the quantity of approximately half the weight of the anthocyanoside or of an anthocyanin extract having an anthocyanoside content of 36±5%.

The compositions according to the invention can be administered topically, for example as water/oil emulsions, aseptic dusting powders or occlusive formulations. According to a preferred aspect, the occlusive formulations will be in solid form, designed to be hydrated at the time of application, and will contain alginic acid as gelling polysaccharide.

The preferred excipients for use in the formulations are polysaccharides, such as hyaluronic acid, chondroitin sulphate or alginic acid, which help to form a protective film that stimulates wound healing.

The formulations are applied to the wound, and the formulation is left to absorb. Particularly infected wounds should be covered with a sticking plaster. The treatment is repeated one to three times a day, taking care to protect the wound or sore against mechanical traumas.

The compositions according to the invention will be prepared according to well-known conventional methods, such as those described in "Remington's Pharmaceutical Handbook", Mack Publishing Co., N.Y., USA, together with suitable excipients.

The following examples illustrate the invention in detail.

EXAMPLE 1

Aqueous Gel

| | |
|---|---|
| *Vaccinium myrtillus* (36% anthocyanosides) | 0.50 g |
| *Echinacea angustifolia* (root extract) | 0.25 g |
| Polyethylene glycol 400 | 5.00 g |
| Glycerin | 5.00 g |
| Carbomer | 1.00 g |
| Sodium hydroxide 10% solution | 2.00 g |
| Sodium bisulphite | 0.20 g |
| Propylparaben | 0.05 g |
| Potassium sorbate | 0.15 g |
| Purified water q.s. for | 100 g |

EXAMPLE 2

Cream (O/W Emulsion)

| | |
|---|---|
| *Vaccinium myrtillus* dried extract | 1.00 g |
| *Echinacea angustifolia* (root extract) | 0.25 g |
| Liquid paraffin | 8.000 g |
| Stearic acid | 10.000 g |
| Sodium sulphite | 0.5 g |
| Polysorbate 80 | 2.000 g |
| Glycerin | 12.000 g |
| Purified water q.s. for | 100.000 g |

EXAMPLE 3

Effect on Ulcers Caused by Venous Stasis of the Lower Limbs 50 patients (10 in each group) suffering from ulcers of the lower limbs caused by venous stasis, not complicated by other vascular disorders, were included in the study.

The patients were treated with the preparation described in example 1, applied to the lesion in amounts of 2 cm (corresponding to 1 g) twice a day. The treated lesions were then covered with a bandage to ensure that the gel was not removed, and to protect them against external agents and/or mechanical traumas. The lesions were monitored for 21 days, and re-epithelialisation was assessed by measuring the two diameters.

Results expressed as the mean of the two diameters measured

The results are set out in the table below.

| TREATMENT | RE-EPITHELIALISATION | | |
|---|---|---|---|
| | 7 days | 14 days | 28 days |
| Placebo | 0.02 ± 0.01 | 0.01 ± 0.01 | 0.03 ± 0.02 |
| Preparation example 1 | 2.14 ± 0.73** | 4.9 ± 1.01** | 8.30 ± 1.10** |
| Placebo + *Vaccinium myrtillus* 0.3% | 0.10 ± 0.03 | 0.23 ± 0.13* | 0.50 ± 0.23* |
| Placebo + *Echinacea angustifolia* 0.3% | 0.01 ± 0.01 | 0.20 ± 0.02* | 0.35 ± 0.02* |

*$P < 0.05$;
**$p < 0.001$ Student's "t" test

In the treatment of radiation dermatitis, the repair time of the damage caused by the radiation in situ is evaluated: the most frequent types of radiation dermatitis are those which occur in the treatment of head, neck, breast, uterus and prostate tumours. In these last cases, radiation treatment causes ulcers over large areas, and the treatment cycle must be discontinued if rapid re-epithelialisation is impossible.

For example, in the case of tumours of the salivary glands, complete remission of the primary lesion in the external cervico-facial zone took place in 48 hours, competed with at least a week in normal oncological practice.

It was also surprisingly found that the formulations according to the invention reduce the regression time of proctitis induced by radiotherapy by 500% compared with untreated controls and patients given conventional treatment.

The invention claimed is:

1. A method of treating peripheral ulcers, radiodermitis induced by radiotherapy and chemotherapy, ulcerated haemorrhoids, proctitis and vulvovaginitis in a subject in need thereof, said method comprising:
    administering an effective amount of a composition comprising:
    a) bisulphite adducts of anthocyanosides from *Vaccinium myrtillus,*
    b) a lipophilic extract of *Echinacea* sp., to a subject in need thereof; and
    treating said subject.

2. The method according to claim 1, wherein the ulcers are diabetic ulcers, ulcers of the limbs due to venous stasis, ulcers due to radiation or mechanical or thermal injuries and bedsores.

3. The method according to claim 1, wherein the composition further comprises anthocyanosides from *Vaccinium myrtillus.*

4. The method according to claim 3, wherein the ulcers are diabetic ulcers, ulcers of the limbs due to venous stasis, ulcers due to radiation or mechanical or thermal injuries and bedsores.

* * * * *